United States Patent [19]

Feinmann et al.

[11] Patent Number: 4,677,139
[45] Date of Patent: Jun. 30, 1987

[54] MATERIAL AND METHOD FOR DENTISTRY

[76] Inventors: Bernhard P. P. Feinmann, 18, Ch. William Barbey, CH-1292 Chambery, Switzerland; Mario Martignoni, Via Maria Adelaide 5, Rome, Italy

[21] Appl. No.: 734,430

[22] Filed: May 16, 1985

Related U.S. Application Data

[60] Division of Ser. No. 618,809, Jun. 8, 1984, abandoned, which is a continuation of Ser. No. 480,985, Mar. 31, 1983, abandoned.

[30] Foreign Application Priority Data

Apr. 7, 1982 [CH] Switzerland .......................... 2138/82

[51] Int. Cl.⁴ .............................................. C08L 83/06
[52] U.S. Cl. .................... 523/111; 128/90; 128/156
[58] Field of Search ................... 523/111; 128/90, 156

[56] References Cited

U.S. PATENT DOCUMENTS

| | | | |
|---|---|---|---|
| 3,082,526 | 3/1963 | Nitzsche et al. | 32/15 |
| 3,082,527 | 3/1963 | Nitzsche et al. | 32/17 |
| 3,228,055 | 1/1966 | Levenson | 15/244 |
| 3,271,332 | 9/1966 | Bond | 521/154 |
| 3,399,457 | 9/1968 | Hagman | 32/19 |
| 3,572,330 | 3/1971 | Gander | 523/111 |
| 3,950,300 | 4/1976 | Hittmair et al. | 260/37 SB |
| 4,230,820 | 10/1980 | Maschberger | 521/154 |

FOREIGN PATENT DOCUMENTS

| | | |
|---|---|---|
| 754052 | 3/1967 | Canada . |
| 754051 | 3/1967 | Canada . |
| 1163021 | 10/1955 | Fed. Rep. of Germany . |
| 572323 | 1/1958 | Italy . |
| 841825 | 7/1956 | United Kingdom . |
| 798669 | 12/1956 | United Kingdom . |
| 867619 | 1/1959 | United Kingdom . |
| 1492581 | 11/1977 | United Kingdom . |

OTHER PUBLICATIONS

Data Sheet: SILASTIC(R) Foam Wound Dressing, Dow Corning Europe, Medical Products Division, Brussels Belgium, 2 pages.
Data Sheet: Prosthetic Products, SILASTIC(R) 386 Foam Elastomer w/catalyst, Dow Corning Corporation, Midland, Mich, 5 pages, Mar. 1976.
Data Sheet: "SILASTIC(R) Brand 390 Soft Liner", Dow Corning Corporation, Midland, Mich. Brochure No. 14-007 (4 pages).
"Report On SILASTIC(R) Brand 390 Soft Liner For Dentures", Peyton, et al., Project Contract-ORA 63-942-B1, Univ. of Michigan, 9/30/83, (13 pages).
"Literature References Pertaining to Development of SILASTIC(R) 390 Soft Liner", Dow Corning Corporation, Broch. CPO-441, 6/64, (9 pages).

*Primary Examiner*—Robert A. Wax
*Attorney, Agent, or Firm*—Richard E. Rakoczy

[57] ABSTRACT

An elastomeric foam composition is useful in dentistry for separating the gingiva from the adjacent teeth, for cleaning, as a pressure pack and wound dressing and as a cushion between dental appliances and the gums of a dental patient. The composition is made from a paste-like system of components which expands at least about 150% to produce a uniformly fine-grained foam composition having a resistance to compression such that a force of at least about 50 g per square cm. is required to result in 10% deflection. In a preferred embodiment, the elastomeric foam composition is formed from a system of components which includes silicone fluids, siliceous fillers, crosslinkers, hydrogen, sources and a catalyst, all present in amounts which provide a paste-like consistency before foaming and a resistance to compression after foaming such that 80 g. per square cm. is required to produce a 10% deflection.

3 Claims, 10 Drawing Figures

MATERIAL AND METHOD FOR DENTISTRY

This Application is a division of pending U.S. Ser. No. 06/618,809, filed June 8, 1984, now abandoned, which is a continuation of U.S. Ser. No. 06/480,985, filed on Mar. 31, 1983, now abandoned.

BACKGROUND OF THE INVENTION

This invention relates to the treatment of dental patients using a foam material. The treatment includes retraction of gingival margins, cushioning dental appliances, cleaning of tooth surfaces and the dressing of wounds in the mouth.

Although dentistry is a technically advanced art there remain areas in need of improvement and problems which require solutions.

One such area is the retraction of the gingival margin in preparation for subsequent subgingival curettage or for the taking of dental impressions. The management of the gingival tissue prior to the taking of a precise impression for prosthetic laboratory work has been among the most difficult procedures in dentistry. The tissue next to the working site must be pushed away from the prepared borders and, if possible, reduced in site.

Many different materials and methods have been used for this work including electrosurgical trophying, the pressing in of restriction rings, copper tubes, retraction sleeves, gingitage (trophying with rotary diamond points), vascularconstrictor-containing retraction cords, astringent substances contained in retraction cords, vascular-constrictor and/or astringent-containing gels and pellets, and the like.

These methods and materials of the prior art have been successful to varying degrees in accomplishing the preparation of gingival tissue for subsequent procedures. However, most of these materials have accompanying disadvantages. For example, the prior art methods and materials may result in sulcus borders which are not complete and not smooth. In other cases there is a substantial risk of postoperative tissue loss with aesthetically unsatisfying results. In some cases continual bleeding of the gums makes it difficult to take impressions. There are often manual difficulties for the dentist in using some of the prior art materials and procedures. Other of the prior art methods result in increased cardiovascular risk and sometimes in severe and lasting postoperative pain.

There are other needs in the field of dentistry which have not been adequately met in the past and which would benefit from new materials and methods. Although toothbrushing and the use of dental floss have long been accepted as means for cleaning teeth and stimulating gums, it would be an improvement to find a material or method which provided improved cleaning of tooth surfaces, especially at intricate shapes and in close passages between teeth and/or fixed prosthetic parts.

There has also been a long-felt need in the dental profession for a cushion material to fit between dental appliances and irritated gums. Such a material, which promotes heating and is readily applicable by the wearer of the appliance, would be especially useful.

There has also been a long-felt need in the dental profession for a more practical wound dressing which can be used in the mouth. Normal gauze and cloth bandages are not comfortably useful in a dental subject's mouth for long periods of time. Normal dental peridontal pressure packs become hard when wet so that they only protect the wound and do not apply a uniform pressure. Foam dressings, such as Dow Corning's SILASTIC ® Foam Dressing, are known for use in open, granulating wounds. However, the system of components used to generate this foam dressing has a viscosity which, when first mixed, is not sufficiently high to be normally desirable in a respiratory pathway and the resulting foam composition is not sufficiently resistant to compression to meet the needs of dentistry described above. This prior art foam dressing also has the disadvantage of an unpleasant taste. Such prior art foams are described in greater detail in British Pat. Nos. 798,669 and 867,619.

It is known from British Pat. No. 841,825 to use a non-foaming silicone room temperature vulcanizing composition for making dental impressions.

It is known from U.S. Pat. No. 3,399,457 to use a rigid foam to form a permanently deformable bite block.

SUMMARY OF THE INVENTION

It is, therefore, an object of this invention to obtain separation of the gingival border from the adjacent tooth.

It is a further object of this invention to obtain improved cleaning of tooth surfaces. It is also an object of this invention to place a cushion between a dental appliance and the gum against which it is worn.

It is still another object of this invention to place a foam dressing in open wounds in the mouth.

It is also an object of this invention to place an improved pressure pack on dental wounds.

It is another object of this invention to present a foam composition for dental use having a desirable resistance to compression after foaming and a paste-like consistency before foaming.

It is also an object of this invention to overcome the disadvantages of the prior art.

These and other objects are accomplished by a biocompatible elastomeric foam composition which is useful in dentistry. The foam is developed from a paste-like system of components such that after a volume expansion of at least about 150%, a uniformly fine-grained foam material is obtained. The foam composition has a resistance to compression such that a force of at least about 50 g. per square cm. applied against one side results in a 10% deflection of the material. In a preferred embodiment, such a force of about 80 g. per square cm. results in a 10% deflection.

The paste-like consistency of the system of components and the resistance to compression of the resulting foam composition give this new composition surprising and unexpected utility in dentistry over known materials, making new methods of treatment possible.

This new foam composition may be used in a process for temporarily separating the gingiva from the adjacent tooth in the mouth of a dental patient. The process includes the steps of placing the components of the system at the margin between the gingiva and the tooth, placing a carrier over the components to contain the foam as it is developed by the components, maintaining the developed foam in pressure contact with the margin for a period of time, and removing the foam from contact with the margin.

Subsequent treatment of the tooth may be accomplished after the foam is removed such as gingival curettage or the taking of a dental impression.

When the foam composition is formed in contact with a tooth surface, it may be used in another aspect of the present invention to clean the tooth surface by causing relative motion between the tooth surface and the foam. Such relative motion may be accomplished by a chewing or swallowing motion made by the dental patient.

In yet another aspect of the present invention the components of the foam are placed on the surface of a dental appliance which is normally in contact with a dental patient's gums and the appliance is placed against the gum while the foam is developed from the system of components.

In still another aspect of the present invention the components of system are placed in a wound in the mouth of a dental patient and the foam is allowed to develop in the wound. The developed foam is maintained in the wound during healing.

THE DRAWINGS

The invention will now be described with reference to the accompanying drawings wherein FIG. 1 shows the prior art method wherein the tooth is prepared down to the gingival sulcus by means of a rotating drill.

DETAILED DESCRIPTION

Figure 1:
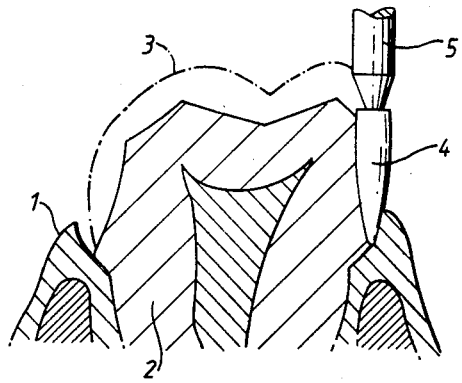

Referring more specifically to FIG. 1 there is shown a prior art method of separating gingival margin 1 from dentin 2 during a procedure in which the surface 3 of the tooth prior to preparation is removed in preparation for subsequent capping with an artificial material.

Removal of surface 3 and the pushing back of gingival margin 1 is accomplished by means of cutting surface 4 which is controlled by drill shank 5.

The prior art method, which is known in gingitage, has the disadvantage that it bruises margin 1, often causing it to bleed and swell, making the subsequent taking of good impressions difficult.

Figure 2:
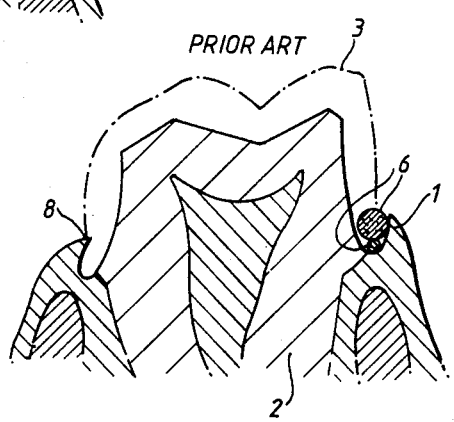
FIGS. 2, 3 and 4 show the prior art method wherein retraction threads are used to separate the gingiva from the adjacent tooth.
Figure 3:
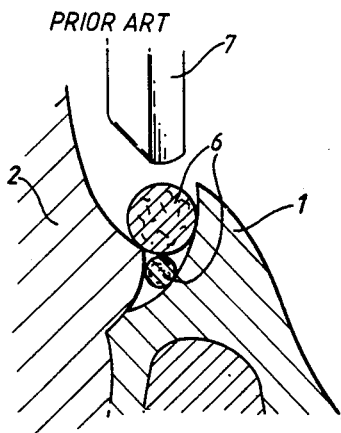
Figure 4:
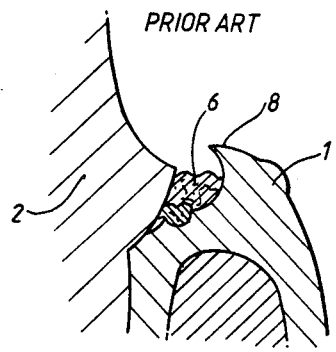

Referring more specifically to FIGS. 2, 3 and 4 there is shown another prior art method of pushing back gingival margin 1 from dentin 2. As in FIG. 1, dentin 2 has had tooth surface 3 removed in preparation for subsequent capping.

Retraction threads 6 of various sizes are used to separate gingival margin 1 from dentin 2. FIG. 3 shows in enlarged cross-section threads 6, which may be impregnated with a vascularconstrictive chemical being pressed into the space between the gingival margin 1 and dentin 2 with dental instrument 7. FIG. 4 shows in enlarged cross section the condition of threads 6 after being pressed into place by instrument 7. FIG. 4 also shows a tip portion 8 of margin 1 which is beginning to curl or "rebound" in the direction of tooth base 2. The extent of the rebound is shown by tip portion 8 in FIG. 2 after threads 6 have been removed. The rebound of tip portion 8 after retraction threads 6 have been removed is a problem of this prior art method in that it makes subsequent treatments, such as the taking of impressions, difficult.

Figure 5:
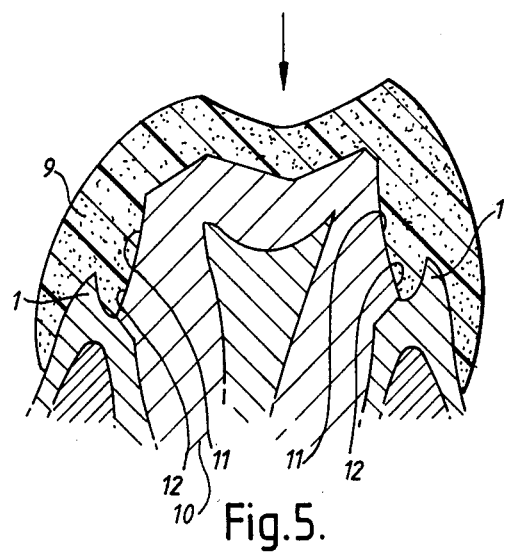
FIG. 5 shows the present invention wherein foam is used to compress the sulcus and gingiva.

Referring more specifically to FIG. 5 there is shown an embodiment of the present invention wherein foam material 9 has been formed over tooth 10 to separate tooth surface 11 from gingival margin 1. The foam is held against tooth 10 and margin 1 by a downward force as shown by the arrow. The force may be applied by, for example, an opposing tooth or by a dental instrument.

It can be seen in FIG. 5 that gingival margins 1 are uniformly compressed and separated from tooth surface 11. Surprisingly, it has been observed that margin 1 retains its compressed shape and its separation from tooth surface 11 for a period of time sufficient to enable subsequent procedures such as the cleaning of portion 12 of surface 11 which is normally covered by margin 1 or the taking of an impression of the tooth using a dental impression material. It is further observed that there is no "rebound" effect shown by the tip of the gingival margin and that there is no accompanying swelling or pain when the present invention is used. Cleaning portion 12 and the taking of impressions, both of which are facilitated by the present invention are procedures which will be well known to one of orindary technical skill in the dental art and need not be detailed here.

Foam composition 9 is developed from a system of components which, when mixed together and applied to the tooth and gum, will flow into the normal space between tooth surface 11 and margin 1 under only slight pressure applied by the dentist or by the dental patient. As the foam develops while being held in place by a suitable carrier, as is desribed in greater detail in connection with FIG. 8, the portion of the system of components which flowed between margin 1 and surface 11 creates a foam which presses margin 1 away from surface 11.

Foam 9 may be formed from any useful material. To be useful a material should be tissue compatible and non-toxic and the development of foam 9 from a system of components should not result in the evolution of a toxic or offensive gas. Suitable materials are silicones, thicol rubbers, polyvinylethers, hydrocoloids and algenates.

Especially good results have been obtained using a silicone elastomer foam which is made from a system of components comprising silicone fluids, siliceous fillers, a crosslinker, a source of hydrogen and a catalyst. In order to be useful in the present invention these components must be combined in relative ratios such that the combined system of components has a paste-like consistency and so that the resulting elastomeric foam has sufficient resistance to compression to be useful. The surprising and unexpected results which provide the technical advantage for the present elastomeric foam over the elastomeric foams of the prior art (such as the aforementioned Dow Corning SILASTIC® Foam Dressing) are believed to result from the relative ratios of the components.

For example said silicone elastomeric foam composition of the present invention has been found to display a useful paste-like consistency and to display a useful resistance to compression in the developed foam only when its components are combined in certain ratios. Said silicone elastomeric foam is useful in the present invention when the system of components from which it is developed includes from about 190 to about 210 parts by weight of silicone fluids; from about 85 to about 110 parts by weight of a siliceous filler; from about 12 to about 16 parts by weight of a crosslinker; from about 18 to about 22 parts by weight of a hydrogen source, and from about 45 to about 55 parts by weight of a catalyst. Optionally, the system of components may contain colorants and flavorings.

It has been observed that whenever the ratio of components varies from the above ratios in silicone elastomeric foam the usefulness of the material diminishes. Such a variance results in the system of components losing its paste-like consistency and in the developed foam having a resistance to compression which is not useful in the desired applications.

The resistance to compression of the composition of the present invention was measured by loading a force against the end of a foam cylinder measuring 2.5 cm in length and 3.5 cm in diameter. Loading was increased until a 10% deflection occurred. Generally speaking, a 50 g. per square cm. loading is required to cause such a deflection in foams useful in the present invention. For comparison, an identically shaped sample of a foam composition made from Dow Corning SILASTIC® Foam Dressing, which is not sufficiently resistant to be used in the present invention, required only 10 g per square cm to obtain a 10% deflection. Foams which require less than 50 g. per square cm. to achieve a 10% deflection in this test have a diminished usefulness in the present invention. The presently preferred embodiment, described below, requires an 80 g. per square cm. loading to achieve a 10% deflection in this test.

In order to be useful in this invention, a minimum expansion of about 150% is required of a foam material in addition to the resistance to compression described above. The expansion, in accordance with the resistance, apparently enables the elastomeric foam to act as is described in FIGS. 5-10. The volume expansion of foams is readily measured by placing the system of components in a graduated cylinder and calculating the volume of the starting material against the volume of the finished foam.

Foams, which show greater volume expansion than 150% but do not develop the necessary resistance to compression, are not useful in the present invention.

Another aspect in which the above-described silicone elastomeric foam demonstrates a surprising and unexpected technical advance over the prior art is in the mixing and curing time. For example, the preferred embodiment, described below, provides a curing time of about four minutes between mixing and curing which gives the dental practitioner an appropriate time to position the system of components after mixing.

A preferred embodiment of the above-described silicone elastomeric foam is made from a system of components which comprises a first component formed from 95 to 105 parts by weight of a —OH terminated polydimethylsiloxane polymer; from 52 to 63 parts by weight of a siliceous filler; from 9 to 11 parts by weight of an —SiH functional silicone fluid, from 9 to 11 parts by weight of a low-viscosity hydroxyfunctional polydimethylsiloxane fluid; from 9 to 11 parts by weight of diphenylmethylsilanol; from 3 to 5 parts by weight of normal propylorthosilicate, and from 7-9 parts by weight of a white pigment. The second component is formed from 95 to 105 parts by weight of a trimethyl terminated polydimethyl siloxane fluid having a viscosity of about 12,500 centistokes; from about 35 to about 45 parts by weight of a siliceous filler; from about 45 to about 55 parts by weight stannous octoate; from about 1.5 to about 2.5 parts by weight of a pink pigment, and from about 0.1 to about 0.2 parts by weight of a flavoring.

The first and second components are prepared separately and stored in tubes. The orifices of the tubes are adjusted in size so that equal length strips of the first and second components may be extruded onto a mixing surface while maintaining the correct relative ratio of components. The strips are then combined, as by a spatula, and immediately placed into position for foam development.

In the preferred embodiment the colored pigment is placed only in one component. The dental practitioner or patient may then understand from a uniformly colored mixture that the components are evenly dispersed. Uniform blending of the two components is important to obtain a uniformly textured foam composition.

Figure 6:
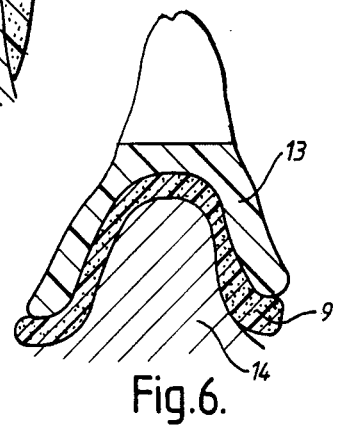
FIG. 6 shows the present invention wherein foam provides a cushion between a dental appliance and the gum.

Referring more specifically to FIG. 6 there is shown dental appliance 13 mounted on gum 14 and having foam material 9 acting as a cushion therebetween. In this embodiment of the invention, foam material 9 is formed by first placing a system of components onto the side of appliance 13 which would normally contact gum 14. Appliance 13 is then mounted on gum 14 while foam 9 is allowed to develop. This application of the present invention is especially suitable when gum 14 is sore or irritated.

Figure 7:
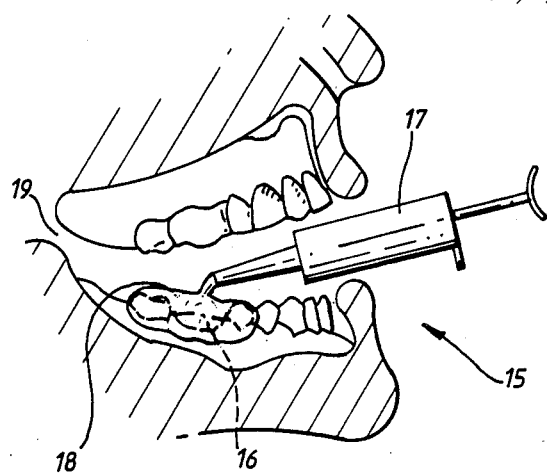
FIG. 7 shows the present invention wherein a foam material is applied as a dressing to maintain a blood clot after extraction.

Referring more specifically to FIG. 7 there is shown mouth 15 of a dental subject having open wound 6 resulting from an extraction on the lower jaw. Syringe 17 is being used to place system of components 18 in extraction wound 16. System of components 18 has a paste-like consistency which enables it to fill the shape of open wound 16 without danger of flowing into respiratory passageway 19 of the dental patient. System of components 18, when it cures to an elastomeric foam material will act as a dressing and will also keep the normal extraction blood clot in place to prevent the "dry socket" condition which results whenever an extraction blood clot comes out of place.

It has been observed that system of components 18 develops into a foam material which operates as a wound dressing to promote healing. The wound is maintained in a clean condition, protected from direct contact with the atmosphere or the mouth while the porous nature of the foam draws secretions away from the wound.

The foam wound dressing has the added advantage that it can be removed, cleaned and replaced by the dental subject. As the wound heals and changes shape subsequent foam dressings may be applied by the patient without the intervention of a dental professional.

Syringe 17 is shown as a convenient device for applying system of components 18 to locations in the back of the mouth. Alternatively, system of components 18 could be applied by means of a dental spatula after the base component and the catalyst component had first been mixed together on a plate.

Figure 8:
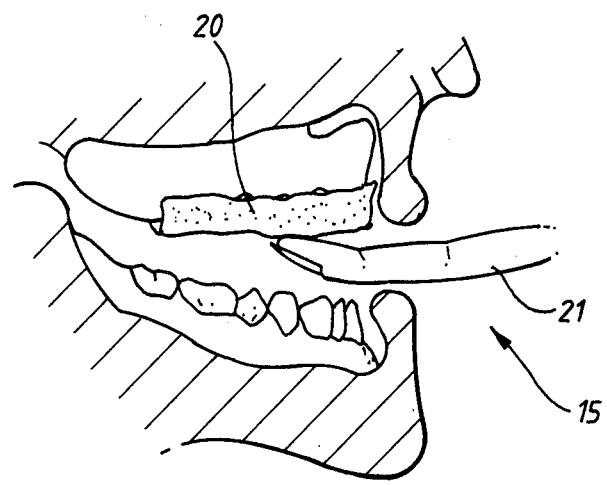
FIG. 8 shows the present invention wherein a carrier is being used to contain the development of a foam around the upper teeth and gums in the mouth of a dental patient.

Referring more specifically to FIG. 8, there is shown mouth 15 of a dental patient in which carrier 20 is being held in place by finger 21 while a system of components under carrier 20 develops into a foam material while being held against the dental subjects upper teeth and gums.

Carrier 20 may be of any useful size or shape and can be made of any suitable material to contain the system of components against the desired surface in mouth 15. For example, a dental instrument may be used for small locations or a spoon can be used.

Figure 9:
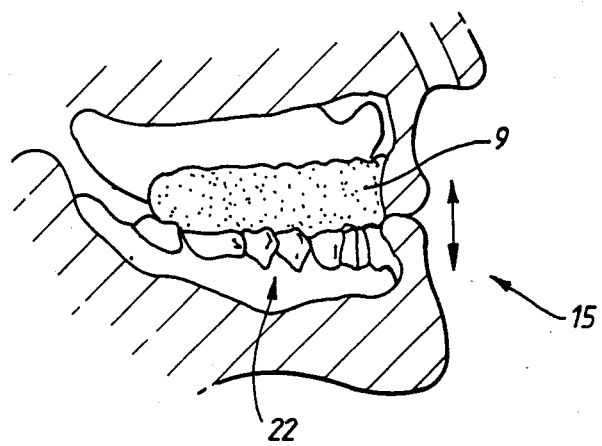
FIG. 9 shows the present invention wherein a developed foam structure is used in cleaning the upper teeth or in separating the gum from the adjacent tooth as is shown in FIG. 5.

Referring more specifically to FIG. 9 there is shown mouth 15 of a dental subject with foam material 9 covering the upper teeth and gums. Foam material 9 of FIG. 9 is of the shape which would have been produced by carrier 20 of FIG. 8.

Foam material 9 of FIG. 9 may be held in place under pressure by lower jaw and teeth 22 for a time sufficient to accomplish the separation of the gingival margin from the tooth surface as is shown in FIG. 5. Experience has shown that such separation can be accomplished by maintaining said pressure for a period of from about 5 to about 10 minutes for the average dental patient. Foam material 9 is then removed to facilitate subsequent procedures.

Alternatively the foam material 9 of FIG. 9 may be moved relative to the surface of the teeth with which it is in contact to accomplish cleaning of said surface. Only small, repeated relative movements are necessary. Such movements can be accomplished by manual manipulation of the foam or, as is shown in FIG. 9 by the arrows, by a chewing action of the lower jaw and teeth 22 against foam material 9.

Figure 10:
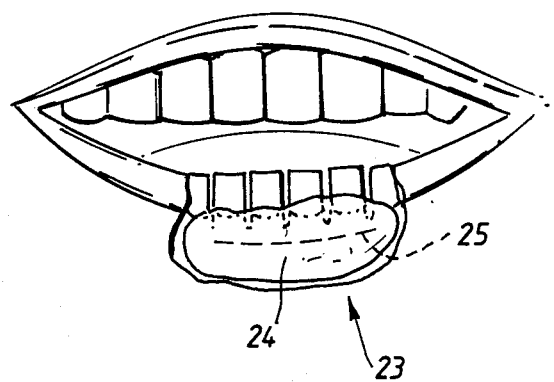
FIG. 10 shows the present invention used as a pressure pack during peridontal intervention.

Referring more specifically to FIG. 10 there is shown a portion 23 of the lower teeth and jaws of a dental patient wherein wound 25 is present resulting, for example, from a tissue grafting procedure. Elastomeric foam composition 24 is shown in use as a pressure pack on wound 25.

Pressure pack 24 is applied by placing the system of components of the present invention into contact with wound 25. Upon curing to an elastomer the pressure pack is held against wound 25 by the pressure of the patient's lip. Unlike the pressure packs of the prior art, pressure pack 24 remains resilient even when wet and distributes pressure uniformly against wound 25. Pressure pack 24 can be removed, cleaned and reinserted and can be replaced, if necessary, by a new foam structure if the shape of the wound changes significantly.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

We claim:

1. A method for forming a foam dressing in a wound in the mouth of a dental patient, the method comprising:
    (a) placing in contact with said wound a biocompatible silicone elastomeric foam composition which is useful in dentistry comprising a paste-like system of components having a viscosity which is sufficiently high to prevent the system of components from flowing into the respiratory airway of the mouth prior to curing, said system of components being curable at body temperature and being capable of undergoing a volume expansion of at least about 150% upon curing to form a uniform, fine-grained, biocompatible, silicone elastomer foam material having a resistance to compression which is such that, after a volume of expansion of at least about 150%, a force of at least 50 g. per square cm. is required to result in a 10% deflection of the foam material; said system of components comprising a first component formed from 95 to 105 parts by weight of a hydroxyl-terminated polydimethylsiloxane polymer; from 52 to 63 parts by weight of a siliceous filler; from 9 to 11 parts by weight of a SiH functional silicone fluid; from 9 to 11 parts by weight of a low-viscosity hydroxyfunctional polydimethylsiloxane fluid; from 9 to 11 parts by weight of diphenylmethylsilanol; and, optionally, from 7-9 parts by weight of a white pigment and a second component formed from 95 to 105 parts by weight of a trimethyl terminated polydimethyl siloxane fluid having a viscosity of about 12,500 centistokes; from about 35 to about 45 parts by weight of a siliceous filler; from about 45 to about 55 parts by weight stannous octoate; optionally from about 1.5 to about 2.5 parts by weight of a colored pigment; and, optionally, from about 0.1 to 0.2 parts by weight of a flavoring;
    (b) allowing the foam material to develop and cure; and
    (c) maintaining the foam material in contact with the wound during healing.

2. The method of claim 1 wherein the dressing is a pressure pack.

3. The method of claim 1 wherein the dressing covers the site of an extraction.

* * * * *